(12) United States Patent
Totman et al.

(10) Patent No.: US 9,108,039 B2
(45) Date of Patent: Aug. 18, 2015

(54) ELECTRODE CONSTRUCTION FOR CREVICE CORROSION PROTECTION

(71) Applicant: Zoll Medical Corporation, Chelmsford, MA (US)

(72) Inventors: Mark Totman, Winchester, MA (US); Pisit Khuon, Providence, RI (US)

(73) Assignee: ZOLL MEDICAL CORPORATION, Chelmsford, MA (US)

(*) Notice: Subject to any disclaimer, the term of this patent is extended or adjusted under 35 U.S.C. 154(b) by 334 days.

(21) Appl. No.: 13/678,008

(22) Filed: Nov. 15, 2012

(65) Prior Publication Data

US 2014/0135887 A1  May 15, 2014

(51) Int. Cl.
*A61N 1/00* (2006.01)
*A61N 1/04* (2006.01)
*A61B 5/0408* (2006.01)

(52) U.S. Cl.
CPC ............ *A61N 1/046* (2013.01); *A61B 5/04087* (2013.01); *A61N 1/0492* (2013.01); *A61B 2562/125* (2013.01)

(58) Field of Classification Search
CPC ... A61N 1/046; A61N 1/0404; A61N 1/0452; A61N 1/0456; A61N 1/048; A61N 1/0492; A61N 1/0472; A61B 5/04087; A61B 2562/125
USPC ........................................................ 607/142
See application file for complete search history.

(56) References Cited

U.S. PATENT DOCUMENTS

| | | | |
|---|---|---|---|
| 5,243,978 A | 9/1993 | Duffin, Jr. | |
| 5,916,244 A * | 6/1999 | Walters | ............... 607/142 |
| 6,148,233 A | 11/2000 | Owen et al. | |
| 7,146,228 B2 * | 12/2006 | Nielsen | ............... 607/142 |
| 2004/0225343 A1 * | 11/2004 | Koike | ............... 607/142 |
| 2007/0196320 A1 | 8/2007 | Yasin | |

OTHER PUBLICATIONS

Association for the Advancement of Medical Instrumentation, ANSI/AAMI DF80:2003 Medical Electrical Equipment—Part 2-4: Particular Requirements for the Safety of Cardiac Defibrillators (including Automated External Defibrillators) 2004, ISBN 1-57020-210-9; abstract; p. vi; p. 50, section 107.1.2.

* cited by examiner

*Primary Examiner* — Michael Kahelin
*Assistant Examiner* — Mallika D Fairchild
(74) *Attorney, Agent, or Firm* — Lando & Anastasi, LLP (57) ABSTRACT

An electrode includes an adhesive backing layer including a front surface configured to adhere to skin of a subject and a rear surface, a plate including a rear surface coupled to the front surface of the adhesive backing layer and a front surface comprising a conductive material layer, a conductive hydrogel including a rear surface coupled to a front surface of the conductive material layer, and including a front surface configured to make electrical contact with the skin of the subject, a dielectric film border formed on the front surface of the conductive material layer and defining an area on the front surface of the conductive material layer, and an electrical lead in electrical contact with the area.

27 Claims, 7 Drawing Sheets

ELECTRODE CONSTRUCTION FOR CREVICE CORROSION PROTECTION

BACKGROUND OF THE INVENTION

1. Field of the Invention

The present invention is directed to medical electrodes, and more particularly, to corrosion resistant transcutaneous electrodes configured to monitor and/or apply therapy to a subject and which may be used with a medical device, such as a defibrillator.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. These efforts are expensive and have a limited success rate, and cardiac arrest, among other conditions, continues to claim the lives of victims.

SUMMARY

In accordance with an aspect of the present invention there is provided an electrode. The electrode comprises an adhesive backing layer having a front surface configured to adhere to skin of a subject and a rear surface, a plate having a rear surface coupled to the front surface of the adhesive backing layer and a front surface that includes a conductive material layer, a conductive hydrogel having a rear surface coupled to a front surface of the conductive material layer, and having a front surface configured to make electrical contact with the skin of the subject, a dielectric film border formed on the front surface of the conductive material layer and defining an area on the front surface of the conductive material layer, and an electrical lead in electrical contact with the area.

In accordance with some embodiments the electrode further comprises an insulating film electrically isolating the area from the conductive hydrogel.

In accordance with some embodiments the insulating film includes borders adhered to the dielectric film border, all borders of the insulating film terminating within a region defined between an inner border of the dielectric film border and an outer border of the dielectric film border.

In accordance with some embodiments a portion of the conductive hydrogel is coupled to the insulating film, and the dielectric film border includes a portion formed on a surface of the conductive material layer at a position between a location where the portion of the conductive hydrogel is coupled to the insulating film and a location where the conductive hydrogel is coupled to the conductive material layer.

In accordance with some embodiments the electrical lead is disposed on the rear surface of the adhesive backing layer and makes electrical contact with the area through a conductive element extending from the area and through the plate and the adhesive backing layer.

In accordance with some embodiments the conductive element comprises an eyelet having a first portion in electrical contact with the electrical lead and a second portion in electrical contact with the enclosed area. The second portion of the eyelet may be disposed entirely within an internal border of the area. The second portion of the eyelet may have a height substantially greater than a height of the dielectric film border.

In accordance with some embodiments the front surface of the plate includes a border free of the conductive material layer.

In accordance with some embodiments the plate comprises an electrically insulating substrate including a front surface upon which the conductive material layer is disposed.

In accordance with some embodiments the plate comprises an electrically conductive substrate.

In accordance with some embodiments the adhesive backing layer, the plate, and the conductive hydrogel are each substantially transmissive to water vapor.

In accordance with some embodiments the electrode is included in a defibrillator.

In accordance with some embodiments the electrode is included in a multi-electrode patch.

In accordance with some embodiments a gap between the conductive hydrogel and the conductive material layer at a location where the conductive hydrogel transitions from contact with the conductive material layer to contact with one of the dielectric film border and the insulating film has a height of less than about 250 microns.

In accordance with some embodiments the electrode is constructed and arranged to remain substantially corrosion free for a time period of at least about two years when maintained at an average temperature of about 35 degrees Celsius.

In accordance with some embodiments the electrode is constructed and arranged to remain substantially corrosion free for a time period of at least about five years when maintained at an average temperature of about 35 degrees Celsius.

In accordance with some embodiments the dielectric film border is shaped as an annulus.

In accordance with some embodiments the dielectric film border is shaped as a multi-sided closed geometric shape.

In accordance with some embodiments the conductive hydrogel extends beyond an outer border of the plate.

In accordance with some embodiments the electrical lead is in electrical contact with a first side of the front surface of the conductive material layer, the conductive hydrogel is in electrical contact with a second side of the front surface of the conductive material layer, and the dielectric film border is formed as a strip disposed on the front surface conductive material layer between the first side of the front surface conductive material layer and the second side of the front surface of the conductive material layer.

In accordance with some embodiments an insulating film is disposed on the first side of the conductive material layer and on a portion of the dielectric film border.

In accordance with some embodiments the conductive hydrogel includes a portion disposed on the dielectric film border.

In accordance with some embodiments the insulating film and the conductive hydrogel are non-overlapping and in other embodiments a portion of the conductive hydrogel overlaps a portion of the insulating film.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

Biomedical electrodes (referred to herein as simply "electrodes") may be used for monitoring various physiological parameters and/or for treating various ailments. For example, electrodes may be used for defibrillating, pacing, cardioversion, and/or monitoring the activity of a subject's heart. The electrodes disclosed herein are suitable for use on human subjects, although use on non-human subjects is also contemplated. Embodiments of electrodes as disclosed herein can be coupled with power sources and control logic to deliver electrical energy to a subject, to determine the timing, levels, and history of applied energy, and to process monitored or detected data for analysis by, for example, a health care provider. Embodiments of electrodes as disclosed herein can may be located proximate to a subject, for example, attached, connected, or coupled to the subject, at an anterior, posterior, lateral, or other location on the subject. For example, embodiments of electrodes as disclosed herein can be attached to the subject's chest, back, side, head, abdomen, torso, thorax, or legs. In some embodiments the electrodes disclosed are external electrodes configured to be attached to the subject proximate to the subject's heart. Embodiments of electrodes as disclosed herein can be disposable or can be configured for repeated use.

In some embodiments, electrodes in accordance with the present invention are less susceptible to corrosion than prior art electrodes. This may provide the electrodes disclosed herein with a longer shelf life and/or with the ability to remain corrosion free while being utilized in an extended-wear scenarios. Electrodes in accordance with the present invention which are less susceptible to corrosion than prior art electrodes may also be more reliable and be less susceptible to failure than prior art electrodes.

Electrodes in accordance with various embodiments of the present invention may be utilized with, for example, an Advanced Life Support (ALS) device, such as the E Series, M Series, R Series, or X Series defibrillators, the Propaq LT, M, or MD monitors or a Basic Life Support (BLS) device, such as the AED Pro or AED Plus defibrillator, each available from Zoll Medical Corporation of Chelmsford Mass. These devices often are provided for emergency use in locations such as offices, restaurants, or other public spaces. These devices may remain unused for extended periods of time, for example, for up to about two years or up to about four years. It is desirable to provide corrosion resistant electrodes for use with such devices so that the electrodes do not corrode and/or malfunction after an extended period of non-use.

Some embodiments of electrodes disclosed herein will remain operational as defined in, for example, standard IEC 60601-2-4: 2010 sections 201.108.1.1, 201.108.1.2, and/or 201.108.1.9, incorporated by reference herein, and substantially or completely corrosion free for time periods in excess of about two years, in excess of about four years, or in excess of about five years when maintained at standard indoor atmospheric conditions (about 20° Celsius and about 70% relative humidity) or at an elevated temperature of, for example, about 35° Celsius on average. Such electrodes may also remain substantially or completely corrosion free and operational after exposure to temperature extremes of, for example, about −30° Celsius or about 65° Celsius for 24 hours or longer. Such electrodes may reduce the need for servicing emergency use defibrillators and/or extend the time period between required servicing and/or reduce the number of electrodes which must be replaced over time, thus reducing the cost of maintaining the emergency use defibrillators in operational condition.

Figure 1:
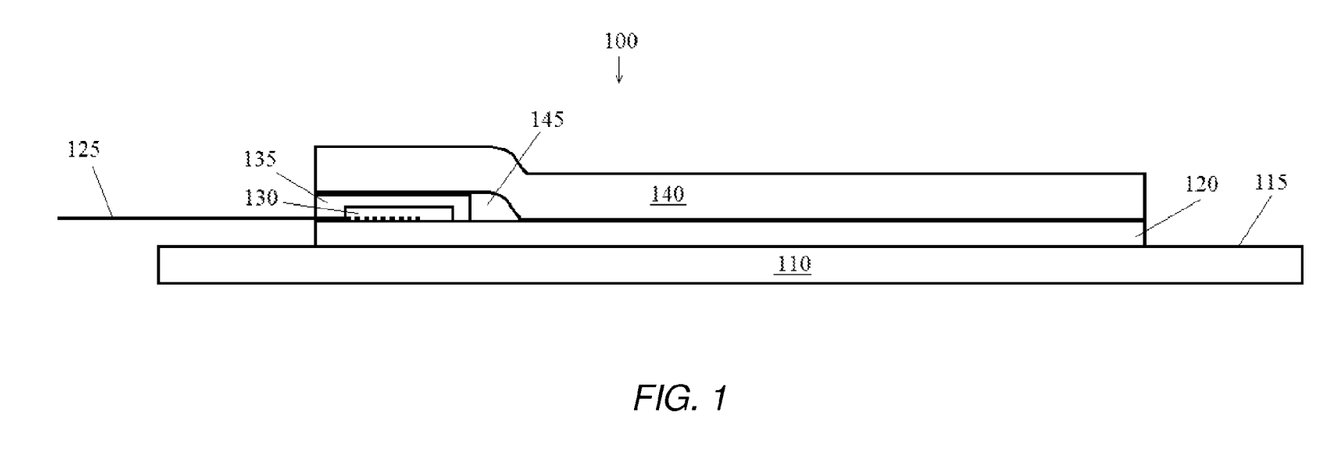
FIG. 1 is a cross sectional view of an electrode.
Figure 4A:
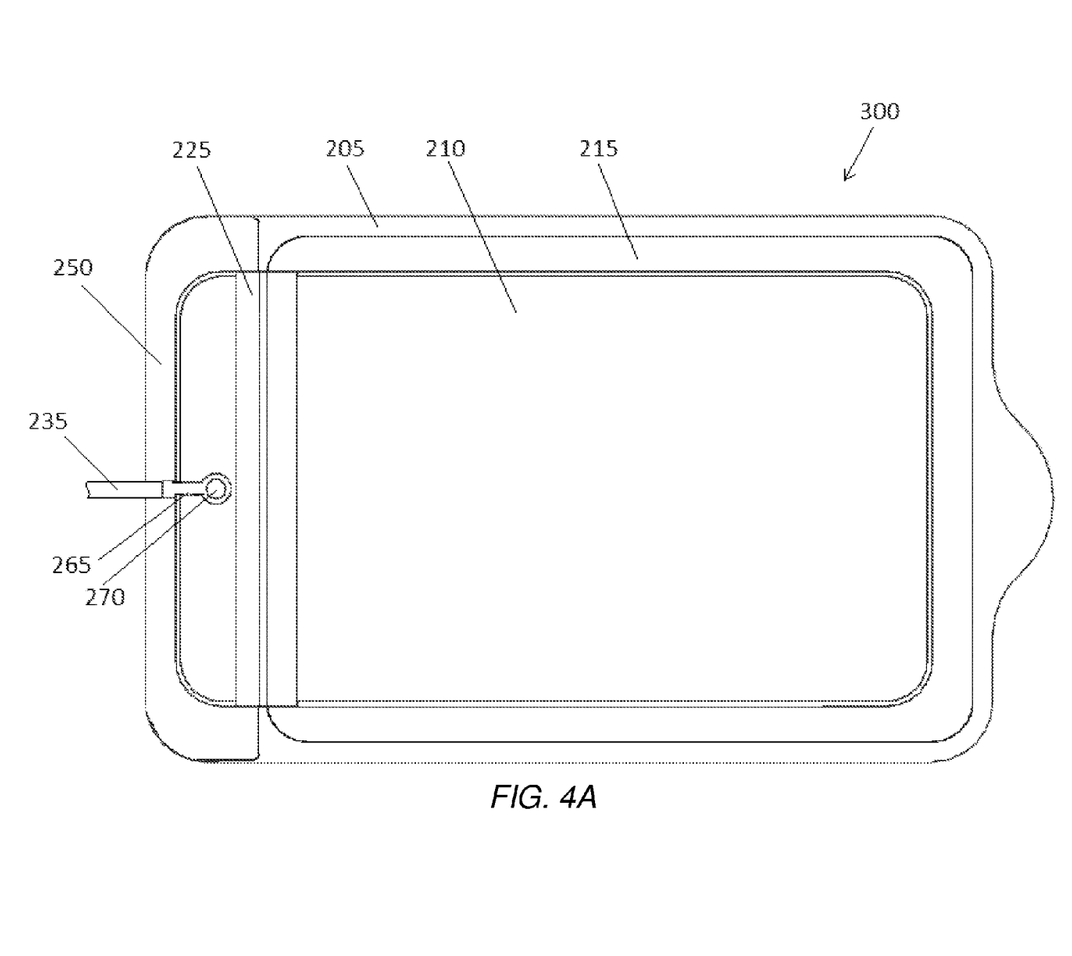
FIG. 4A is a plan view of an electrode in accordance with an embodiment of the present invention.

As illustrated in FIG. 1 and generally indicated at 100, some prior electrode designs may include a backing 110 with an adhesive surface 115. A conductive electrode material 120, for example, a thin film of a metal such as aluminum or tin may be adhered to the adhesive surface of the backing. A wire 125 may be provided conduct electrical energy to the electrode. The wire 125 may be secured to the conductive electrode material 120 by soldering or, as shown, by a press fit tab 130. Alternatively, the wire 125 may be secured to the conductive electrode material 120 by a conductive ring terminal (for example, a ring terminal in a connector 265 as shown in FIG. 4A) coupled to an end of the wire 125 and a corresponding conductive eyelet (for example, eyelet 240 shown in FIGS. 2B and 4B) passing through the ring terminal. Either the ring terminal or the eyelet will include at least a portion in electrical contact with the conductive electrode material 120. A double sided adhesive cover 135 may be placed atop the press fit tab or conductive ring terminal/eyelet connector to secure it in place and to provide an adhesive surface for a conductive hydrogel 140 to adhere. The conductive hydrogel 140 may be placed on the conductive electrode material 120 and adhered thereto, for example, by a conductive adhesive or due to an adhesive property of the conductive hydrogel 140 itself. An air gap 145 may be formed where the conductive hydrogel transitions from contact with the conductive electrode material 120 to contact with the adhesive cover 135. The air gap may have a thickness of, for example, between about 0.01 inches (about 254 microns) and about 0.04 inches (about 1,016 microns). This air gap may form a differential aeration cell which may accelerate corrosion at the junction, which may lead to failure of the electrode to deliver energy when needed.

In some embodiments of electrodes disclosed herein air gaps such as air gap 145 may be substantially reduced or eliminated. A printed dielectric crossover layer may be provided at a transition where a conductive hydrogel transitions from contact with a conductive electrode material such as conductive electrode material 120 to contact with an adhesive cover such as adhesive cover 135. The dielectric layer can be precisely screen printed to achieve a functional thickness of between about 0.001 inches (1 mil, about 25 microns) and about 0.002 inches (2 mils, about 51 microns) or greater, resulting in a decreased height for the gel to traverse. The dielectric layer may cover a portion of the conductive electrode material which might otherwise be exposed to an air gap where the conductive hydrogel transitions from contact with the conductive electrode material to contact with the adhesive cover. This portion of the conductive electrode material would thus be shielded from exposure to the air gap and would be significantly less susceptible to corrosion.

In some embodiments, an air gap between the conductive hydrogel and the conductive electrode material at a location where the conductive hydrogel transitions from contact with the conductive electrode material to contact with the dielectric crossover layer or the adhesive cover has a height of less than, for example, about 250 microns, and in some embodiments less than, for example, about 50 microns or about 25 microns.

Figure 2A:
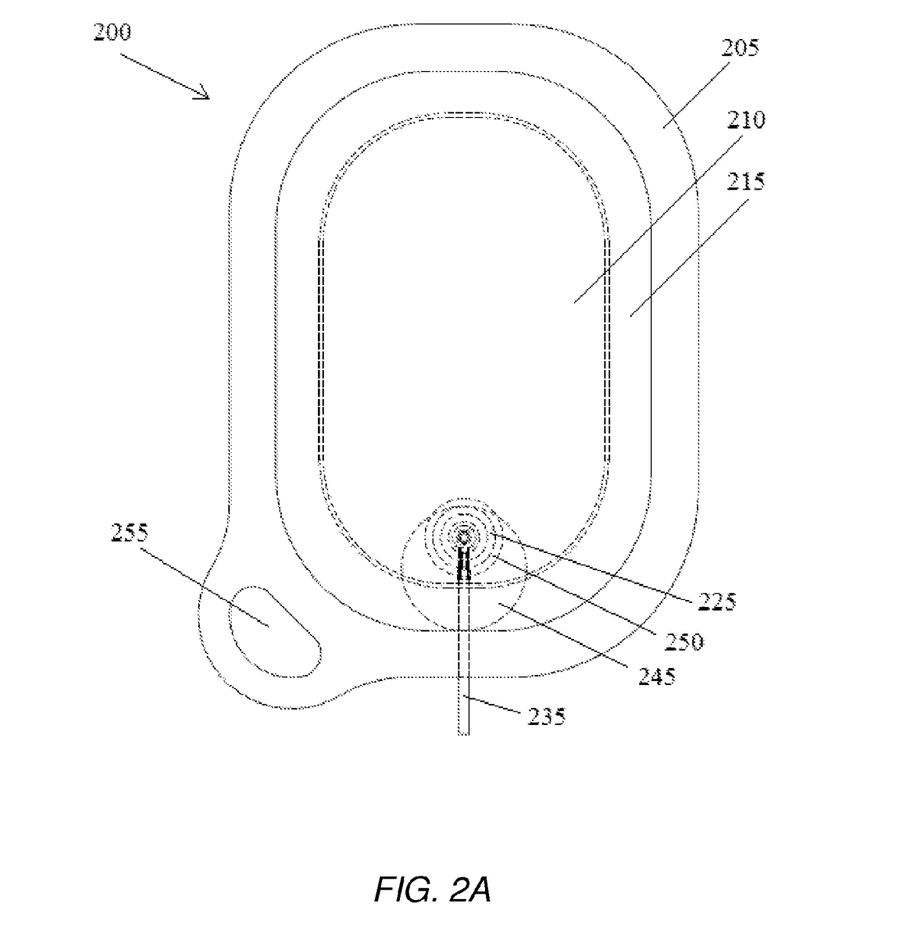
FIG. 2A is a plan view of an electrode in accordance with an embodiment of the present invention.
Figure 2B:
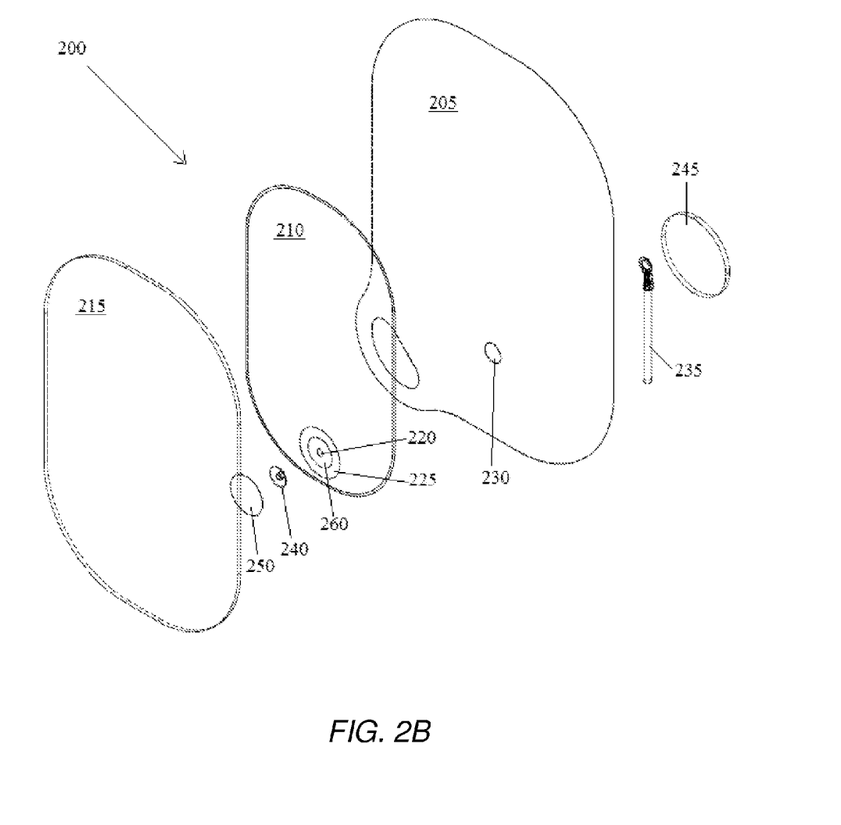
FIG. 2B is an exploded view of the electrode of FIG. 2A.

A generalized illustration of an embodiment of an electrode in accordance with the present invention, indicated generally at 200, is shown in plan view in FIG. 2A and in an exploded view in FIG. 2B. The electrode 200 is a multiple layer laminated structure including an adhesive backing 205, a conductive plate 210, and a conductive hydrogel 215. The conductive plate 210 may include a through-hole 220 which may be surrounded by a dielectric film border 225. The dielectric film border 225 is illustrated in FIGS. 2A and 2B in the shape of an annulus, although the dielectric film border 225 may in various embodiments be formed in the shape of any desired geometric figure. The dielectric film border 225 may be formed as a closed geometric figure or an open geometric figure. The conductive plate 210 may include a conductive material which is contiguous over a front surface (a surface which would face a subject when the electrode was applied to the subject) of the conductive plate. The dielectric film border 225 may be formed atop the front surface of the conductive material. The conductive material may extend beneath the dielectric film border 225 and have a thickness beneath the dielectric film border 225 consistent with the thickness of the conductive material at other locations on the conductive plate 210. The dielectric film border 225 may cover a portion of the conductive material and shield this portion of the conductive material from exposure to air or other materials of the electrode, thus reducing the potential for corrosion of this portion of the conductive material.

The adhesive backing 205 may include a through-hole 230 which may substantially align with the through-hole 220 of the conductive plate when the electrode is assembled. An end of a conductive lead or wire 235 positioned on a back side (a side facing away from a subject when the electrode is applied to the subject) of the adhesive backing 205 may make electrical contact through the through-holes 220 and 230 with an eyelet or grommet 240 positioned at least partially atop a front surface of the conductive material of the conductive plate 210. The eyelet may be formed of a conductive material and may provide an electrically conductive path between the conductive material of the conductive plate 210 and the conductive lead or wire 235. The conductive lead or wire 235 may be electrically coupled to the eyelet 240 by, for example, a snap fitting, a ring terminal which electrically and mechanically mates with the eyelet 240, by soldering, by being adhered in place by other components of the electrode 200, or by other methods known in the art. An adhesive insulating film 245 may be provided to adhere the conductive lead or wire 235 to the rear surface of the adhesive backing 205.

The conductive lead or wire 235 may in use communicate with an external circuit which may utilize the electrode for monitoring, pacing, and/or defibrillating a subject's heart. In other embodiments, the electrode may include or be coupled to circuitry which communicates wirelessly with an external control and/or monitoring circuit. Although not depicted in FIG. 2A or 2B, the conductive lead or wire 235 may be physically and electrically connected to a connector, which may then be connected to and disconnected from external circuitry by a mating connector, each of which may be waterproof. Alternatively, the conductive lead or wire 235 may be formed from a material, such as gold, which can withstand exposure to the elements and repeated connections to and disconnections from the external circuitry.

A strain relief (not shown) may be used to hold the conductive lead or wire 235 in a fixed position with respect to the adhesive backing 205.

A second adhesive insulating film 250 may be provided to insulate the eyelet 240 from the conductive hydrogel 215. The conductive hydrogel 215 may be electrically insulated and physically separated from all conductive portions of the electrode 200 (for example, the conductive lead or wire 235 or the eyelet 240) except for the conductive material of the conductive plate 210. The second adhesive insulating film 250 may also facilitate maintaining the eyelet in electrical contact with the conductive material of the conductive plate 210.

In some embodiments, the adhesive backing layer 205 may be formed from a polymeric material, for example low density polyethylene (LDPE). The adhesive backing layer 205 is in some embodiments substantially non-conductive such that electrical current cannot pass from the conductive plate 210 or conductive hydrogel 215 through the adhesive backing layer 205. The adhesive backing layer 205 may be provided with a relatively large, easy-to-grip pull tab 255 to facilitate handling of the electrode 200.

In some embodiments, the conductive plate 210 is formed of a conductive material, for example, a thin metal plate. In other embodiments, the conductive plate 210 includes a substrate upon which a conductive material has been deposited. The substrate for the conductive plate 210 may include a conductive material or a non-conductive material. The substrate for the conductive plate 210 may include a polymeric film or plate, for example a thin plate of polyethylene terephthalate (PET) or another polymer. The substrate may have a thickness of, for example, about 4 mils (about 100 microns). A conductive layer may be deposited on the substrate for the conductive plate 210 on a side of the substrate intended to contact the conductive hydrogel 215 by any of various methods known in the art, for example, by physical vapor deposition (evaporative deposition or sputtering), screen printing, electrodeposition, or by painting with a conductive ink. The conductive material may include a thin layer of a metal, for example, a mixture or an alloy of aluminum, tin, copper, and/or one or more other metals or metal alloys. The conductive material may be a conductive polymer or a conductive ink, for example, a conductive ink including silver (Ag) and silver chloride (AgCl) such as ECM ink # CI-4002A, available from Engineered Conductive Materials, LLC of Delaware, Ohio. The conductive material may have a thickness of, for example, from about 1.4 mils to about 1.6 mils (from about 36 microns to about 41 microns). The conductive plate 210 may have dimensions of about 2.25 inches (5.72 cm) wide by about 3.75 inches (9.52 cm) high. In some embodiments a thin border area having a thickness of, for example, about 0.03 inches (about 0.08 cm) about the edge of the conductive plate 210 on which the conductive material is deposited may be free of conductive material. The conductive plate 210 may include perforations to facilitate the passage of water vapor from a subject's skin therethrough.

The dielectric film border 225 may be formed atop the conductive material of the conductive plate 210 and define an enclosed area 260 on the top surface of the conductive material. The dielectric film border 225 may be formed by any of various methods known in the art, for example, by chemical vapor deposition, screen printing, or by painting. The dielectric film border 225 may be formed from a substantially non-conductive ink, for example, Electrodag 1020A available from Henkel AG & Co. of Düsseldorf, Germany or another non-conductive ink. The dielectric film border 225 may have a thickness of, for example, from about 1.2 mils to about 1.6 mils (from about 30 to about 41 microns). The dielectric film border 225, when formed as a ring or annulus, may have an outer diameter of, for example, about 0.63 inches (about 1.6 cm) and an inner diameter of, for example, about 0.38 inches (about 0.97 cm). The dielectric film border 225 may be formed in shapes other than a ring, for example, a triangle, square, or other shape.

Figure 3A:
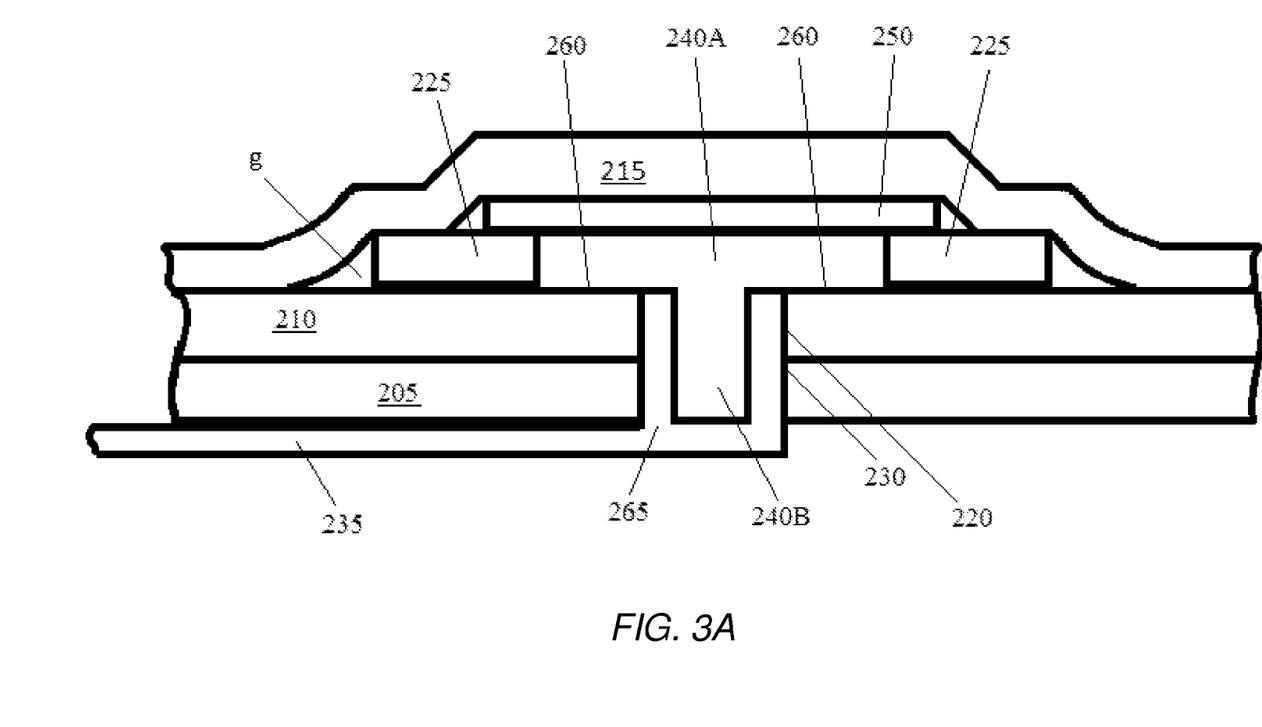
FIG. 3A is a cross sectional view of a portion of an embodiment of the electrode of FIG. 2A.

The eyelet 240 may have a portion in contact with the conductive material which is entirely disposed within, or in some embodiments, substantially coextensive with the enclosed area 260 defined by the inner diameter of the dielectric film border 225. As illustrated in FIG. 3A, which is a partial cross-section of the electrode of FIGS. 2A and 2B through a portion of the electrode including the eyelet and dielectric film border 225, the eyelet may have an upper portion 240A which substantially covers the enclosed area 260 and which may be electrically coupled to conductive material of the conductive plate in the enclosed area 260. The upper portion 240A of the eyelet 240 may extend substantially or completely between portions of a surface or surfaces defining the inner diameter or inner border(s) of the dielectric film border 225. This configuration may preclude the formation of any air gaps between the eyelet 240, the dielectric film border 225, and the upper surface of the conductive plate 210. The elimination of any air gaps between the eyelet 240, the dielectric film border 225, and the upper surface of the conductive plate 210 may reduce the potential for corrosion of the material of the eyelet or of the conductive plate as compared to alternate designs including an air gap in this portion of the electrode. In other embodiments, however, the eyelet 240 may have a portion in contact with the conductive material which is not coextensive with the enclosed area 260 defined by the inner diameter of the dielectric film border 225 so that a spacing is defined between at least a portion or the entirety of a wall of the eyelet and the inner diameter of the dielectric film border 225.

A lower portion 240B of the eyelet may extend through the plate 210 and adhesive backing layer 205 and form a snap fitting with a connector 265 electrically coupled to the conductive lead or wire 235. The snap fitting may include a male portion formed from the portion 240B of the eyelet as illustrated, or a male portion formed from the connector 265 and a corresponding female portion formed in the potion 240B of the eyelet.

As illustrated in FIG. 3A, the upper portion of the eyelet may have a height substantially similar to that of the dielectric film border 225. In other embodiments, the upper portion of the eyelet may have a height greater than or less than that of the dielectric film border 225.

Figure 3B:
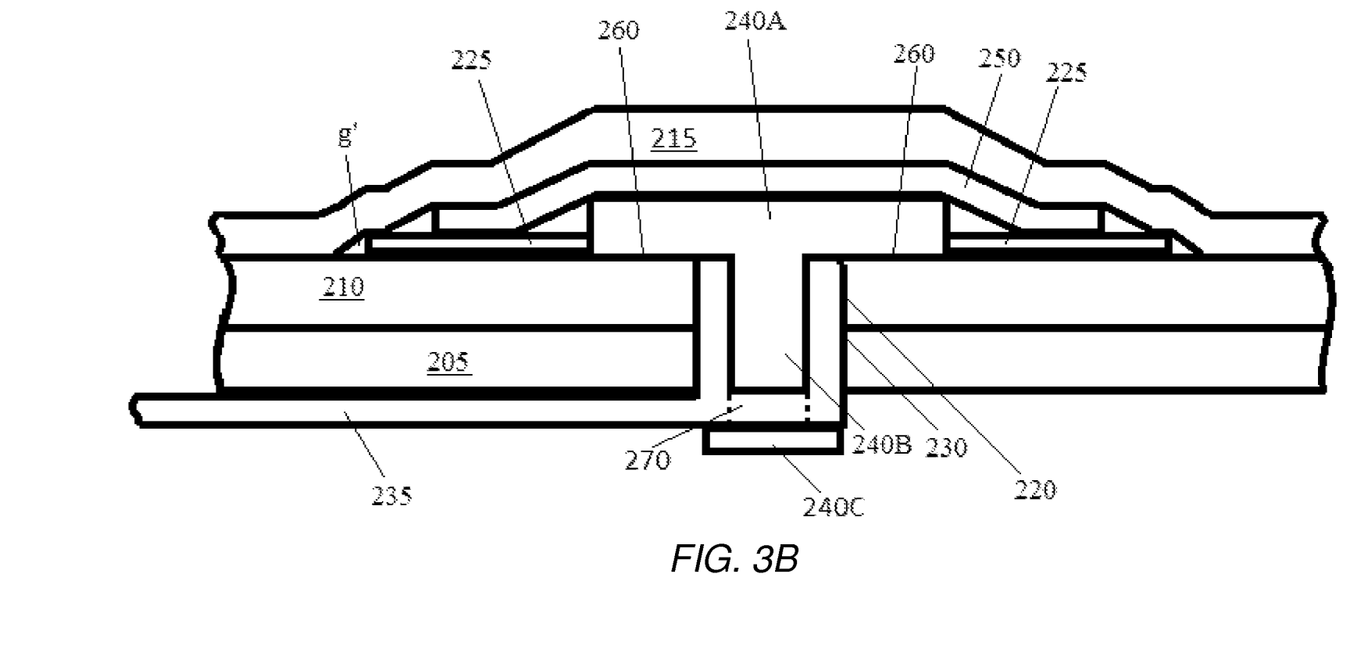
FIG. 3B is a cross sectional view of a portion of an embodiment of the electrode of FIG. 2A.

For example, as illustrated in FIG. 3B, the dielectric film border 225 may have a height substantially less than that of the upper portion 240A of the eyelet 240. The upper portion 240A of the eyelet 240 may have a height of, for example, about ten times that of the dielectric film border 225. Comparing air gap g of FIG. 3A with air gap g' of FIG. 3B, it can be seen that providing a thinner dielectric film border 225 reduces the size of an air gap that may form where the conductive hydrogel 215 transitions from atop the dielectric film border 225 to atop the conductive plate 210. Even the air gap g of FIG. 3A is smaller than the air gap 145 of the electrode of FIG. 1 due to the provision of the dielectric film border 225.

As also illustrated in FIG. 3B, the lower portion 240B of the eyelet 240 may extend through a ring terminal or aperture 270 in the connector 265 electrically coupled to the wire 235. The lower portion 240B of the eyelet 240 may form a flange 240C about the lower portion of the aperture in the connector 265 to facilitate retaining the eyelet in place and in electrical communication with the wire 235 and conductive plate 210.

As further illustrated in FIGS. 3A and 3B, the adhesive insulating film 250 may be applied atop the eyelet 240 to facilitate holding the eyelet in place against the conductive plate 210. The adhesive insulating film 250 may electrically insulate the conductive hydrogel 215 from the eyelet 240 so that the conductive hydrogel 215 makes electrical contact with no portions of the electrode other than the conductive material of the conductive plate 210. When the dielectric film border is formed as a ring, the adhesive insulating film 250 may be substantially circular and have a diameter intermediate between the inner diameter of the dielectric film border 225 and the outer diameter of the dielectric film border 225 such that a border of the adhesive insulating film 250 does not extend beyond an outer border of the dielectric film border 225. Similarly, if the dielectric film border 225 is formed in a different shape, such as a square or triangle, the adhesive insulating film 250 may be sized and shaped to extend past an inner border of the dielectric film border 225, but not past an outer border of the dielectric film border 225. This arrangement of the adhesive insulating film 250 above the eyelet 240 and dielectric film border 225 may provide a substantially smooth profile above they eyelet 240 which may facilitate the conductive hydrogel 215 to extend over the adhesive insulating film 250, eyelet 240, and dielectric film border 225 without passing over any significantly abrupt edges. Providing for the conductive hydrogel 215 to extend over these features without passing over abrupt edges reduces the probability of the formation of air gaps between the conductive hydrogel and the adhesive insulating film 250, eyelet 240, dielectric film border 225, or conductive plate 210.

With renewed reference to FIG. 2A, the conductive plate 210 may have a surface area less than that of the conductive hydrogel 215. In some embodiments, the conductive hydrogel 215 may include borders which extend beyond the borders of the conductive plate by, for example, about 0.25 inches (0.65 cm). The conductive hydrogel 215 may have a surface area less than that of the adhesive backing layer 205 although in some embodiments, portions or all of the conductive hydrogel 215 may extend beyond the borders of the adhesive backing layer 205. When the electrode is assembled, the conductive plate 210 may be entirely enclosed between the conductive hydrogel 215 and the adhesive backing layer 205. In other embodiments the conductive hydrogel 215 and conductive plate may be substantially coextensive with one another. The adhesive backing layer 205 may have portions extending beyond the border of the conductive hydrogel 215 to provide adhesion to the skin of a subject on all sides about the border of the conductive hydrogel 215. The adhesive backing layer 205 may confine the conductive hydrogel 215 and prevent conductive hydrogel from escaping from an area covering the surface of the conductive plate 210 or from beneath the adhesive backing layer 205.

The conductive hydrogel 215 included in electrodes in accordance with various embodiments disclosed herein may include a conductive polymer hydrogel, gel pad, gel sponge, or conductive fluid. The conductive hydrogel 215 may be adhesive to skin. The conductive hydrogel 215 may comprise a material that may be applied to the skin of a subject for extended-wear time periods of greater than, for example, about a week and up to about two weeks without causing significant skin irritation in areas where the conductive hydrogel 215 contacts the skin of the subject. The conductive hydrogel 215 may be a hydrogel such as described in U.S. Provisional Patent Application No. 61/653,749 filed May 31, 2012 and titled LONG TERM WEAR MULTIFUNCTION BIOMEDICAL ELECTRODE a copy of which is attached hereto as Appendix A.

Figure 4B:
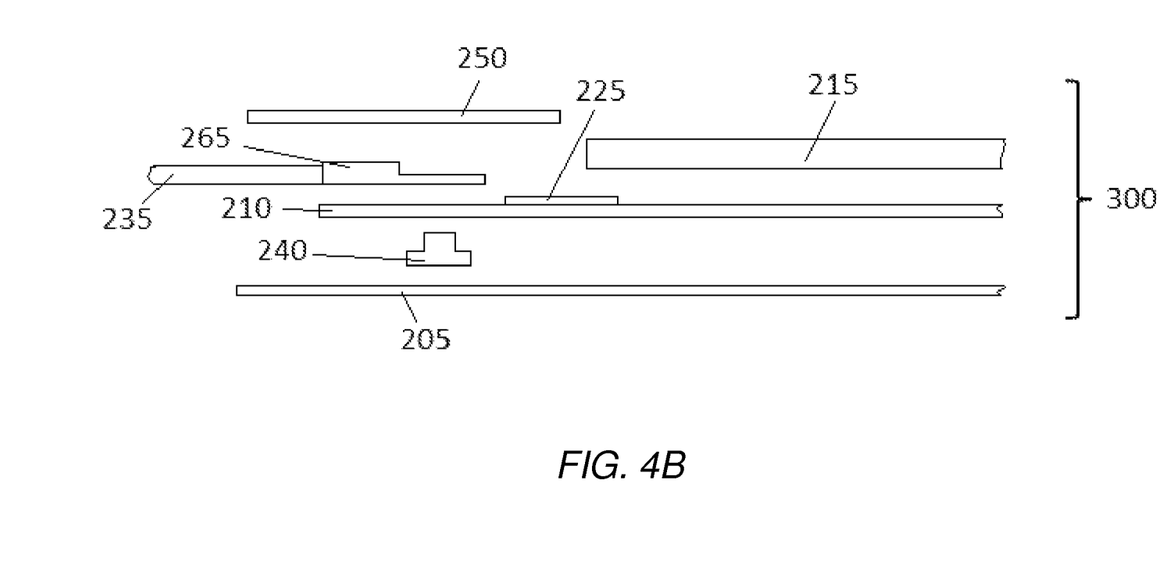
FIG. 4B is an exploded cross sectional view of a portion of the electrode of FIG. 4A.

An alternate configuration for an electrode in accordance with an embodiment of the present invention is illustrated in plan view generally at 300 in FIG. 4A and in a partial exploded cross sectional view in FIG. 4B. In the embodiment of the electrode 300, like components are given like reference numbers as in the electrode 200 discussed above.

In electrode 300 the wire 235 is electrically coupled to a connector 265, which may include a ring terminal as illustrated or any other electrical connector appropriate for making electrical contact with the conductive plate 210. The connector 265 makes electrical contact with a first side of an upper surface of the conductive plate 210. The connector 265 may be held in place in contact with the conductive plate 210 by one or more of an eyelet 240 which passes through a ring terminal in the connector 265 (see FIG. 4B) and an adhesive insulating film 250. Instead of forming a ring or other geometric shape defining a closed area 260 on the surface of the conductive plate as in the electrode 200 described above, the dielectric film border 225 may be formed atop the conductive material of the conductive plate 210 in the form of a strip between the first side of the conductive plate to which the connector 265 is coupled, and a second side of the conductive plate upon which the conductive hydrogel 215 is disposed. As further illustrated in FIGS. 4A and 4B one or both of the adhesive insulating film 250 and the conductive hydrogel 215 may at least partially overlap the dielectric film border 225. Although illustrated as non-overlapping in FIG. 4A, in some embodiments, the conductive hydrogel 215 may overlap a portion of the adhesive insulating film 250. Further, in some embodiments, the wire 235 and connector 265 may be disposed on a lower surface of the conductive plate 210 rather than an upper surface as illustrated, and the eyelet 240 may be disposed on the upper surface of the conductive plate 210.

The electrodes 200, 300 are illustrated as having a rounded rectangular shape, however, other shapes are also contemplated. For example, an electrode 200 may have a substantially circular shape with a substantially circular conductive plate 210, a substantially circular conductive hydrogel layer 215, and a substantially circular adhesive backing layer 205. The present invention is not limited to any particular shape of an electrode or of the components thereof and any one or more components of an electrode in accordance with the present invention may have different shapes than those illustrated. For example, an electrode or one or more of the components thereof may be oval, triangular, square, pentagonal, or any other shape desired. The overall shape of any one or more of the conductive plate 210, conductive hydrogel layer 215, and/or the adhesive backing layer 205 may differ from one another.

Electrodes in accordance with the present invention may include additional features not illustrated, for example, adhesive layers bonding the various components of the electrode together, labeling, a mechanism for holding the electrical conductor in place and in electrical contact with the conductive plate, and/or packaging. Exemplary additional features are disclosed in co-pending U.S. patent application Ser. No. 13/079,336, titled BIOMEDICAL ELECTRODE, which is herein incorporated by reference in its entirety for all purposes. Components of electrodes in accordance with embodiments of the present invention may be formed from materials having certain desirable properties. For example, an electrode may be formed of materials that render it radiolucent or radiotransparent, as disclosed in co-pending U.S. patent application Ser. No. 13/079,336. Further, although not depicted in the figures, electrodes in accordance with the present invention may communicate wirelessly with other circuitry.

Electrodes in accordance with the present invention may be substantially flat. For example, electrodes 200, 300 may have a flat profile that is not noticeable or is minimally noticeable when attached to the subject, under the subject's clothes. Electrodes 200, 300 may also be substantially flexible. For example, electrodes 200, 300 can conform to the contours of a subject's body during initial attachment to the subject, and can conform to body positioning changes when the subject is in motion. Electrodes 200, 300 can also be substantially devoid of rigid components, such as hard snaps, connectors, and rigid plates. For example, electrodes 200, 300 may be devoid of hard rigid substances that may cause uncomfortable pressure points when a subject with an electrode 200, 300 attached to his/her body is in a prone, prostrate, supine, or lateral position with an electrode 200, 300 pressed against an object, such as a bed, couch, medical examining table, clothes, or medical equipment.

The surface area of the conductive hydrogel layer 215 which contacts the skin of the subject may be varied in accordance with various factors such as, for example, the surface area of the conductive plate of the electrode, the magnitude of the current and/or voltage to be delivered to the subject, or the magnitude of the signal to be monitored. For example, the surface area of the conductive hydrogel layer 215 may be larger when the electrode is intended to deliver an electric charge for defibrillation or cardioversion to a subject than when the electrode is designed to monitor or pace a subject. A larger surface area, for a given conductivity of the conductive hydrogel layer 215, would decrease the current density of electricity applied to the subject, thus reducing the potential for electrical burns and/or discomfort of the subject. In other embodiments, where the electrode is intended to deliver charge to a subject in a precise location, the conductive hydrogel layer 215 may be formed with a smaller surface area. The conductivity of the conductive hydrogel layer 215 may also be a factor is determining an appropriate surface area of the conductive hydrogel layer 215. The surface area and the conductivity of the conductive hydrogel layer 215 are factors in determining the total impedance of the conductive hydrogel layer 215. In some embodiments, the surface area of the conductive hydrogel layer 215 may be from about 50 cm$^2$ (7.75 in$^2$) to about 250 cm$^2$ (38.75 in$^2$) total (e.g., 125 cm$^2$ per electrode in a two electrode system) for the electrodes in an electrode system, although this area may vary depending upon the purpose of the electrode(s) and the conductivity of the conductive hydrogel layer 215. In electrode systems including multi-electrode patches, each individual electrode segment may be circular, and have a radius from about 1.22 cm (4.7 cm$^2$ in area) to about 1.73 cm (9.4 cm$^2$). Electrode systems including multi-electrode patches may have total electrode surface areas of as small as about 37.5 cm$^2$ (5.8 in$^2$) to about 75 cm$^2$ (11.6 in$^2$). A multi-electrode patch may include electrodes having a total surface area which is significantly smaller than the effective surface area of the electrodes. The effective surface area of the electrodes is the surface area of a single electrode patch which would perform equivalently for the delivery of electric charge to a subject as the multi-electrode patch.

Different functions of the electrode may be preferentially performed with electrodes having different impedances. As used herein, the impedance of an electrode is defined as the impedance between a conductive element of the electrode and the skin of the subject to which the electrode is attached, and including any conductive hydrogel layer disposed between the conductive element and the subject's skin. For example, when used for defibrillation, an electrode may desirably have a low impedance of less than about three Ohms. When used for defibrillation, the combined impedance of an electrode system including two electrodes, any conductive hydrogel, and the subject (to whom the electrode system is attached) will typically be less than about 200 Ohms when measured during a defibrillation event or during the application of a low energy pulse used to measure the subject's impedance. It should be appreciated that the combined impedance of the electrode system and the subject may vary depending on the impedance of the subject, the size and type of electrode (e.g., a segmented or non-segmented electrode), the type of hydrogel or other conductive gel used, etc. Generally, the distribution of impedances for such a combined electrode system and subject may vary from about 20 Ohms to about 200 Ohms, although ranges of between about 50 Ohms to about 175 Ohms, or between about 85 Ohms and about 115 Ohms may be more common.

When used for pacing, the impedance may desirably be higher to facilitate a reduction in a subject's discomfort, for example, between approximately 30 Ohms to approximately 100 Ohms or more. When used for pacing, the combined impedance of an electrode system including two electrodes, any conductive gel, and the subject will typically be between about 100 Ohms to about 300 Ohms, or more. When used for monitoring, the impedance may desirably be low, for example, three Ohms or less, so that weak electrical signals from a subject with a low signal-to-noise ratio can be accurately sensed. One or both of the conductive gel layer conductivity and surface area may be varied to obtain a desired impedance. The conductive gel layer of electrodes in accordance with the present invention may be formed of a material which gives the electrode an impedance that will satisfy the impedance requirements set forth in the ANSI/AAMI DF80: 2003 medical electrical equipment standard for the safety of cardiac defibrillators.

Electrodes in accordance with some embodiments of the present invention may be used in syncope monitoring and/or treatment devices such as described in U.S. Provisional Patent Application No. 61/653,857 filed May 31, 2012 and titled SYSTEMS AND METHODS FOR DETECTING HEALTH DISORDERS a copy of which is attached hereto as Appendix B.

Embodiments of the present invention may include two or more electrodes combined into a single electrode unit or patch and sharing a common adhesive film layer. Example of patches including multiple electrodes are disclosed in U.S. Provisional Patent No. 61/653,749 attached hereto as Appendix A. When combined in a multi-electrode patch, individual electrodes may perform different functions, for example, one or more of pacing, monitoring, defibrillating, and cardioversion and may have characteristics, for example, surface area or conductivity, which are tailored for the particular function(s) the individual electrodes are intended to perform.

In various instances it may be desirable to pace and/or monitor the heart of a subject with non-invasive, externally placed electrodes for an extended period of time, for example, while the subject is recovering from a heart attack, surgery, or other injury to the heart, while awaiting a heart transplant, or to monitor and/or protect a subject at risk of syncope. In some prior art externally-attached biomedical electrodes, attachment of the electrodes to the skin of a subject may result in skin irritation at the point of attachment within a relatively short period of time ranging, for example, from about a few hours to about a few days. Electrodes in accordance with embodiments of the present invention are constructed of materials, for example, adhesive films and conductive hydrogels which may reduce the occurrence of skin irritation and/or extend the time for which the electrode may be comfortably attached to the skin of a subject.

In some embodiments, extended-wear electrodes in accordance with the present invention may be worn continuously by a subject for a time period in excess of, for example, three days, for a week or more, or for up to about two weeks or more without the subject experiencing significant skin irritation due to the attachment of the electrode to the skin of the subject. As used herein "significant skin irritation" is defined as corresponding to a skin irritation grading of one (a weakly positive reaction usually characterized by mild erythema and/or dryness across most of the treatment site) or more as set forth in Table C.1 of Annex C of AANI/AAMI/ISO standard 210993-10:2010 when electrodes are tested on human subjects in accordance with the method set forth in this standard.

In some embodiments, extended-wear electrodes in accordance with the present invention may facilitate the reduction in skin irritation when used for extended-wear regimens by providing for the passage of water vapor, for example, from a subject's sweat through the electrode. Electrodes in accordance with the present invention may exhibit a moisture vapor transmission rate (MVTR) of, for example between about 600 $g/m^2/day$ and about 1400 $g/m^2/day$ when worn by a subject in an environment at room temperature and at a relative humidity of, for example, about 70%.

For example, in some embodiments, the adhesive backing layer 205 may be formed from a flexible, waterproof, yet breathable material that permits the passage of water vapor away from the subject. Suitable materials may include, for example, polyurethane or Tegaderm™ wound care dressings (3M, St. Paul, Minn., USA) or other non-woven polymers.

The substrate of the conductive plate 210 may in some embodiments be formed of a natural or synthetic fabric, for example, cotton, wool, or polyester. Forming the substrate out of a fabric material may provide for the substrate to easily conform to the contours of the body of a subject. Forming the substrate out of a fabric material may facilitate passage of water vapor from a subject's skin through the substrate.

Embodiments of electrodes in accordance with the present invention may be utilized with a wearable medical device, for example, a LifeVest® wearable cardioverter defibrillator available from Zoll Medical Corporation (Chelmsford, Mass.) or may be directly adhered to the skin of a subject at desired locations. The electrodes may be connected to external monitoring and control electronics located at a convenient position, for example, attached to a subject's belt. Embodiments of electrodes in accordance with the present invention may be used with other devices, for example, a BLS or an ALS device, such as the AED Pro or AED Plus defibrillator, a ProPaq M.D., Propaq LT, or Propaq M, X Series defibrillators, M Series defibrillators, R Series defibrillator BLS, or E Series defibrillators manufactured by the Zoll Medical Corporation.

Any of the above referenced dimensions, and any other dimensions referred to herein as examples may vary in various embodiments. The embodiments of the present invention are not limited to any particular dimensions for any of the components thereof. The various features of the embodiments described herein may be combined or substituted as desired.

Having thus described several aspects of at least one embodiment of this invention, it is to be appreciated various alterations, modifications, and improvements will readily occur to those skilled in the art. Such alterations, modifications, and improvements are intended to be part of this dis- closure, and are intended to be within the scope of the invention. Accordingly, the foregoing description and drawings are by way of example only.

What is claimed is:

1. An electrode comprising:
an adhesive backing layer having a front surface configured to adhere to skin of a subject and a rear surface;
a plate having a rear surface coupled to the front surface of the adhesive backing layer and a front surface that includes a conductive material layer;
a conductive hydrogel having a rear surface coupled to a front surface of the conductive material layer, and having a front surface configured to make electrical contact with the skin of the subject;
a dielectric film border formed on the front surface of the conductive material layer and defining an area on the front surface of the conductive material layer;
an electrical lead in electrical contact with the area; and
an insulating film electrically isolating the area from the conductive hydrogel, wherein the insulating film includes borders adhered to the dielectric film border, all borders of the insulating film terminating within a region defined between an inner border of the dielectric film border and an outer border of the dielectric film border.

2. The electrode of claim 1, wherein a portion of the conductive hydrogel is coupled to the insulating film, and wherein the dielectric film border includes a portion formed on a surface of the conductive material layer at a position between a location where the portion of the conductive hydrogel is coupled to the insulating film and a location where the conductive hydrogel is coupled to the conductive material layer.

3. The electrode of claim 1, further comprising a conductive element extending from the area and through the plate and the adhesive backing layer, wherein the electrical lead is disposed on the rear surface of the adhesive backing layer and makes electrical contact with the area through the conductive element.

4. The electrode of claim 3, wherein the conductive element comprises an eyelet having a first portion in electrical contact with the electrical lead and a second portion in electrical contact with the area.

5. The electrode of claim 4, wherein the second portion of the eyelet may be disposed entirely within an internal border of the area.

6. The electrode of claim 5, wherein the second portion of the eyelet has a height greater than a height of the dielectric film border.

7. The electrode of claim 6, wherein the front surface of the plate includes a border free of the conductive material layer.

8. The electrode of claim 1, wherein the plate comprises an electrically insulating substrate including a front surface upon which the conductive material layer is disposed.

9. The electrode of claim 8, wherein the front surface of the plate includes a border free of the conductive material layer.

10. The electrode of claim 1, wherein the plate comprises an electrically conductive substrate.

11. The electrode of claim 1, wherein the adhesive backing layer, the plate, and the conductive hydrogel are each transmissive to water vapor.

12. The electrode of claim 1, included in a defibrillator.

13. The electrode of claim 1, included in a multi-electrode patch.

14. The electrode of claim 1, wherein a gap between the conductive hydrogel and the conductive material layer at a location where the conductive hydrogel transitions from contact with the conductive material layer to contact with one of the dielectric film border and the insulating film has a height of less than 250 microns.

15. The electrode of claim 14, constructed and arranged to remain substantially corrosion free for a time period of at least two years when maintained at an average temperature of 35 degrees Celsius.

16. The electrode of claim 15, constructed and arranged to remain substantially corrosion free for a time period of at least five years when maintained at an average temperature of 35 degrees Celsius.

17. The electrode of claim 1, wherein the dielectric film border is shaped as an annulus.

18. The electrode of claim 1, wherein the dielectric film border is shaped as a multi-sided closed geometric shape.

19. The electrode of claim 1, wherein the conductive hydrogel extends beyond an outer border of the plate.

20. The electrode of claim 1, wherein the electrical lead is in electrical contact with a first side of the front surface of the conductive material layer, the conductive hydrogel is in electrical contact with a second side of the front surface of the conductive material layer, and the dielectric film border is formed as a strip disposed on the front surface conductive material layer between the first side of the front surface conductive material layer and the second side of the front surface of the conductive material layer.

21. The electrode of claim 20, further comprising an insulating film disposed on the first side of the conductive material layer and on a portion of the dielectric film border.

22. The electrode of claim 21, wherein the conductive hydrogel includes a portion disposed on the dielectric film border.

23. The electrode of claim 22, wherein the insulating film and the conductive hydrogel are non-overlapping.

24. The electrode of claim 22, wherein a portion of the conductive hydrogel overlaps a portion of the insulating film.

25. An electrode comprising:
an adhesive backing layer having a front surface configured to adhere to skin of a subject and a rear surface;
a plate having a rear surface coupled to the front surface of the adhesive backing layer and a front surface that includes a conductive material layer;
a conductive hydrogel having a rear surface coupled to a front surface of the conductive material layer, and having a front surface configured to make electrical contact with the skin of the subject;
a dielectric film border formed on the front surface of the conductive material layer and defining an area on the front surface of the conductive material layer;
an electrical lead in electrical contact with the area; and
an insulating film electrically isolating the area from the conductive hydrogel,
wherein a gap between the conductive hydrogel and the conductive material layer at a location where the conductive hydrogel transitions from contact with the conductive material layer to contact with one of the dielectric film border and the insulating film has a height of less than 250 microns.

26. The electrode of claim 25, constructed and arranged to remain corrosion free for a time period of at least two years when maintained at an average temperature of 35 degrees Celsius.

27. An electrode comprising:
an adhesive backing layer having a front surface configured to adhere to skin of a subject and a rear surface;

a plate having a rear surface coupled to the front surface of the adhesive backing layer and a front surface that includes a conductive material layer;

a conductive hydrogel having a rear surface coupled to a front surface of the conductive material layer, and having a front surface configured to make electrical contact with the skin of the subject;

a dielectric film border formed on the front surface of the conductive material layer and defining an enclosed area on the front surface of the conductive material layer;

an electrical lead in electrical contact with the enclosed area; and an insulating film electrically isolating the enclosed area from the conductive hydrogel.

* * * * *

UNITED STATES PATENT AND TRADEMARK OFFICE
CERTIFICATE OF CORRECTION

| | | |
|---|---|---|
| PATENT NO. | : 9,108,039 B2 | Page 1 of 1 |
| APPLICATION NO. | : 13/678008 | |
| DATED | : August 18, 2015 | |
| INVENTOR(S) | : Mark Totman et al. | |

It is certified that error appears in the above-identified patent and that said Letters Patent is hereby corrected as shown below:

In the Specification:

Column 4, Line 21, delete "provided conduct" and insert -- provided to conduct --.

Signed and Sealed this
Sixteenth Day of February, 2016

Michelle K. Lee
*Director of the United States Patent and Trademark Office*